United States Patent
Cai

(10) Patent No.: US 11,523,877 B2
(45) Date of Patent: Dec. 13, 2022

(54) POSITION ADJUSTMENT APPARATUS FOR ADJUSTING POSITION OF DETECTION DEVICE AND MAGNETOCARDIOGRAPHY INSTRUMENT

(71) Applicant: Beijing X-Mag Technologies Limited, Beijing (CN)

(72) Inventor: Bin Cai, Beijing (CN)

(73) Assignee: BEIJING X-MAG TECHNOLOGIES LIMITED, Beijing (CN)

( * ) Notice: Subject to any disclaimer, the term of this patent is extended or adjusted under 35 U.S.C. 154(b) by 0 days.

(21) Appl. No.: 17/700,341

(22) Filed: Mar. 21, 2022

(65) Prior Publication Data

US 2022/0304771 A1  Sep. 29, 2022

(30) Foreign Application Priority Data

Mar. 23, 2021 (CN) .......................... 202110307843.6

(51) Int. Cl.
| | | |
|---|---|---|
| *A61B 90/50* | (2016.01) | |
| *A61B 5/00* | (2006.01) | |
| *A61B 5/243* | (2021.01) | |

(52) U.S. Cl.
CPC .............. *A61B 90/50* (2016.02); *A61B 5/243* (2021.01); *A61B 5/704* (2013.01); *A61B 2562/0223* (2013.01); *A61B 2562/046* (2013.01); *A61B 2562/182* (2013.01)

(58) Field of Classification Search
CPC ......... A61B 90/50; A61B 5/243; A61B 5/704; A61B 2090/508; A61B 2090/5025; A61B 2090/504; A61B 2562/0223; A61B 2562/046; A61B 2562/182; A61G 13/06

See application file for complete search history.

(56) References Cited

U.S. PATENT DOCUMENTS

| | | |
|---|---|---|
| 2004/0030324 A1 | 2/2004 | Creighton et al. |
| 2004/0199068 A1 | 10/2004 | Bucholz et al. |
| 2005/0212515 A1 | 9/2005 | Watanabe et al. |
| 2008/0086049 A1 | 4/2008 | Seki et al. |
| 2011/0295103 A1 | 12/2011 | Ichimura et al. |
| 2014/0000630 A1 | 1/2014 | Ford |

(Continued)

FOREIGN PATENT DOCUMENTS

| | | |
|---|---|---|
| CN | 101152083 A | 4/2008 |
| CN | 102048541 A | 5/2011 |

(Continued)

OTHER PUBLICATIONS

Chunsheng, "Design and development of a medical examination vehicle", Nanjing University of Science and Technology, Jiangsu Province 211, Engineering Colleges, 2018, pp. 1-94.

*Primary Examiner* — Sean D Mattson
(74) *Attorney, Agent, or Firm* — Kilpatrick Townsend & Stockton LLP

(57) ABSTRACT

A position adjustment apparatus for adjusting a position of a detection device, and a magnetocardiography instrument are provided. The position adjustment apparatus includes: two support assemblies, a lifting frame, and at least one height adjustment assembly. The position adjustment apparatus of the present disclosure enables free control over the height of the lifting frame by providing support rods and the height adjustment assembly comprising a pulley block.

20 Claims, 12 Drawing Sheets

(56) References Cited

U.S. PATENT DOCUMENTS

| | | | |
|---|---|---|---|
| 2014/0235996 A1 | 8/2014 | Kim et al. | |
| 2015/0164725 A1* | 6/2015 | Wilson | A61G 13/101 128/845 |
| 2016/0360987 A1 | 12/2016 | Miyasaka et al. | |
| 2018/0021003 A1 | 1/2018 | Kim et al. | |
| 2018/0289283 A1* | 10/2018 | Carlsson | A61G 13/06 |
| 2020/0170528 A1* | 6/2020 | Erasala | G01R 33/421 |
| 2020/0196887 A1 | 6/2020 | Burton | |

FOREIGN PATENT DOCUMENTS

| | | |
|---|---|---|
| CN | 104546048 A | 4/2015 |
| CN | 105078502 A | 11/2015 |
| CN | 107157516 A | 9/2017 |
| CN | 108549154 A | 9/2018 |
| CN | 109247990 A | 1/2019 |
| CN | 110200630 A | 9/2019 |
| CN | 110584614 A | 12/2019 |
| CN | 110974264 A | 4/2020 |
| CN | 111562030 A | 8/2020 |
| CN | 211433206 U | 9/2020 |
| CN | 111874073 A | 11/2020 |
| CN | 112472135 A | 3/2021 |

\* cited by examiner

POSITION ADJUSTMENT APPARATUS FOR ADJUSTING POSITION OF DETECTION DEVICE AND MAGNETOCARDIOGRAPHY INSTRUMENT

CROSS-REFERENCES TO RELATED APPLICATIONS

This application claims priority to Chinese Patent Application No. CN 202110307843.6 filed Mar. 23, 2021. The entire contents of CN 202110307843.6 are incorporated by reference herein in its entirety for all purposes.

TECHNICAL FIELD

The present application relates to the field of mechanical structures, and particularly to a position adjustment apparatus for adjusting a position of a detection device and a magnetocardiography instrument.

BACKGROUND OF THE INVENTION

Magnetic images obtained by magnetocardiography (MCG), magnetoencephalography (MEG), etc. are images of magnetic fields that are produced by human organs and detected by using very sensitive sensors. Taking the magnetocardiography as an example, the magnetocardiography is to obtain an image over the chest by non-invasively recording magnetic fields generated by the electric activity of the heart in a cardiac cycle. The magnetocardiography originated in the early 1960s. After many years of development, the MCG technology has progressively matured and has been clinically put into practice. At present, MCG examination has been clinically applied in Germany, Japan, Finland, China, etc.

One of the mainstream magnetocardiography methods is to use a magnetocardiography instrument based on an atomic magnetometer. This magnetocardiography method is inexpensive and requires little maintenance, making a wide range of MCG applications possible.

During use of the magnetocardiography instrument, it is first necessary to put a magnetic field detection device directly above and close to the heart of the human body to be detected. Only at this position can detection data with high quality be obtained. However, for most of current apparatuses capable of conveniently adjusting the position of the magnetic field detection device, electrical devices such as an electric motor need to be used, and the introduction of these electrical devices may generate additional interference magnetic fields, thereby affecting the detection results of the magnetic field detection device or even rendering the magnetic field detection device inoperable. Therefore, it is an important subject and research direction in the art to design a position adjustment apparatus capable of avoiding the use of an electrical device while having a good adjustment effect.

BRIEF SUMMARY OF THE INVENTION

According to one aspect of the present disclosure, the present disclosure provides a position adjustment apparatus for adjusting a position of a detection device, the position adjustment apparatus comprising: two support assemblies, each of the support assemblies comprising at least one support rod; a lifting frame arranged between the two support assemblies, the lifting frame having two ends respectively slidably connected to the support rods of the two support assemblies and being configured to move in a height direction of the support rods, the lifting frame comprising a mounting portion for mounting the detection device; and at least one height adjustment assembly arranged on at least one side of the lifting frame where one of the two support assemblies is located and configured to adjust a lifting height of the lifting frame, each height adjustment assembly of the at least one height adjustment assembly comprising: a first pulley and a second pulley arranged in the height direction of the at least one support rod, and rotating shafts of the first pulley and the second pulley being both fixedly mounted on a support assembly arranged on the corresponding side of the lifting frame; and a drive belt wound around the first pulley and the second pulley, the lifting frame being fixedly connected to a predetermined position on the drive belt, the drive belt being configured to drive the lifting frame to move as the first pulley and the second pulley rotate.

In one example, each height adjustment assembly further comprises a locking mechanism, and the locking mechanism comprises: a fixed toothed disk fixedly arranged on the support assembly on the corresponding side of the lifting frame, wherein a hollow portion for accommodating at least a part of the first pulley is provided in the center of the fixed toothed disk, and a plurality of limiting teeth are arranged on an inside periphery of the hollow portion; and a limiting push piece slidably arranged on the first pulley and configured to slide in a radial direction of the first pulley, and the end of the limiting push piece facing the inside periphery of the hollow portion is further provided with complementary teeth that are complementary with the plurality of limiting teeth.

In one example, the first pulley comprises an inner wheel and an outer rotating disk that are coaxial with each other, wherein the drive belt is wound around the inner wheel and the second pulley, the outer rotating disk is accommodated in the hollow portion, and the limiting push piece is arranged on the outer rotating disk.

In one example, the outer rotating disk is provided with a guide groove for accommodating the limiting push piece and allowing the limiting push piece to slide in a radial direction of the outer rotating disk.

In one example, a plurality of limiting protrusions and limiting recesses cooperating with the plurality of limiting protrusions are respectively provided at edges of two sides of the limiting push piece and an inner side of the guide groove, and the limiting push piece has a first position and a second position that are defined jointly by the limiting protrusions and the limiting recesses, and The locking mechanism is configured such that when the limiting push piece is pushed into the first position, the complementary teeth are meshed with at least some of the plurality of limiting teeth to lock the first pulley; and when the limiting push piece is pushed into the second position, the complementary teeth are separated from the plurality of limiting teeth to release the first pulley.

In one example, a shank is further provided on the limiting push piece.

In one example, the support assembly further comprises: a housing forming a cavity for accommodating the support rods and the height adjustment assembly; and a part of the housing corresponding to the outer rotating disk is provided with an opening for exposing at least a part of the outer rotating disk to the exterior of the housing.

In one example, the rotating shafts of the first pulley and the second pulley are both fixedly arranged on the housing of the corresponding support assembly.

In one example, the outer rotating disk further comprises: a handle arranged on the part of the outer rotating disk exposed to the exterior of the housing to facilitate rotation of the outer rotating disk.

In one example, the two support assemblies comprise a first support assembly and a second support assembly, and the lifting frame comprises: a first end plate slidably connected to the support rod of the first support assembly; a second end plate slidably connected to the support rod of the second support assembly; and at least one cross beam, two ends of each cross beam being respectively connected to the first end plate and the second end plate.

In one example, the height adjustment assembly is arranged on one side of the lifting frame where the first support assembly is located; the first support assembly comprises two support rods arranged in parallel, and the height adjustment assembly is arranged between the two support rods; and the first end plate is fixedly provided with two sets of sleeves at the positions corresponding to the two support rods, and the sleeves of each set of sleeves are respectively fitted outside the corresponding support rods.

In one example, the second support assembly comprises one support rod; and the second end plate is fixedly provided with a set of sleeves at the position corresponding to the support rod, and the sleeves are fitted outside the support rod.

In one example, a damping layer is further provided between the sleeve and the corresponding support rod.

In one example, the first end plate is further fixedly provided with an engagement portion, the engagement portion is provided with a slit allowing the drive belt to pass through, and the engagement portion is fixed to a predetermined position of the drive belt by means of a screw traversing the slit.

In one example, at least a part of an upper surface of each cross beam is arranged tilted downwards in a direction from the first end plate to the second end plate.

In one example, the lifting frame further comprises: at least one structural reinforcing rope, two ends of each structural reinforcing rope being respectively connected to two ends of one cross beam; and the upper surface of the cross beam is further provided with a wire guide groove for accommodating the structural reinforcing rope.

In one example, the lifting frame further comprises: at least two sliding rods arranged in parallel, two ends of each sliding rod being respectively directly or indirectly connected to the first end plate and the second end plate; and the mounting portion further comprises a plurality of sleeves, the plurality of sleeves being fitted on the at least two sliding rods such that the mounting portion slides along the sliding rods.

In one example, the mounting portion further comprises an armrest to facilitate pushing the mounting portion to slide.

In one example, the detection device comprises a plurality of magnetometer probes, the mounting portion further comprises a mounting panel, and the mounting panel is provided with a plurality of slotted holes for mounting the plurality of magnetometer probes.

In one example, the position adjustment apparatus is integrally made of a nonmetallic material.

According to another aspect of the present disclosure, the present disclosure further provides a magnetocardiography instrument, comprising: a bed body; the position adjustment apparatus as mentioned above, bottom ends of the two support assemblies of the position adjustment apparatus being respectively slidably connected to edges of two side in a length direction of the bed body such that the position adjustment apparatus slides in the length direction of the bed body; and a plurality of magnetometer probes mounted on the mounting portion of the position adjustment apparatus.

In one example, the bottom ends of the two support assemblies are further provided with a plurality of rollers; and the bed body is further provided with tracks at the positions corresponding to the bottom ends of the two support assemblies, the tracks extending in the length direction of the bed body for accommodating the plurality of rollers.

In one example, the tracks are arranged on left and right sides of the bed body; and the plurality of rollers are arranged on the sides of the bottom ends of the support assemblies facing the bed body so as to be opposite the tracks.

In one example, the bed body is further provided with a rack extending in the length direction thereof, and the position adjustment apparatus further comprises a limiting mechanism, wherein the limiting mechanism comprises: a cam-knob rotatably arranged on the support assembly and comprising a cam portion and a knob portion that are coaxially connected to the cam portion; and a limiting member provided with a cam hole for engagement with the cam portion, one end of the limiting member extending downwards and facing the rack, and the end being further provided with a plurality of snap teeth cooperating with the rack; wherein the limiting mechanism is configured to control the meshing or separation of the snap teeth and the rack by causing the cam portion to drive the limiting member to move up and down by means of rotating the knob portion.

In one example, the rack is arranged on an upper surface of the track; and the limiting member comprises a first section extending downwards and a second section extending toward the bed body, an end of the second section extends into the track, and an upper surface of the end is provided with the snap teeth.

In one example, the magnetocardiography instrument further comprises: a base for bearing the bed body; and a magnetic shielding cabin arranged on the base, wherein the bed body is further configured to slide in a length direction of the base; and the magnetic shielding cabin is configured to cover the position adjustment apparatus when the bed body slides toward the magnetically shielded cabin to a predetermined position.

The position adjustment apparatus of the present disclosure enables free control over the height of the lifting frame by providing support rods and the height adjustment assembly comprising a pulley block. A user can adjust the height of the detection device by manually rotating a first pulley or a second pulley, and the operation is simple and convenient. In addition, no electrical devices such as an electric motor are provided inside the position adjustment apparatus of this embodiment, and the adjustment of the position of the detection device is completely performed manually, so that it is especially suitable for a detection environment in which the electric devices are not suitable for use.

BRIEF DESCRIPTION OF THE DRAWINGS

In the accompanying drawings, the same reference numerals denote the same or similar parts or elements throughout multiple drawings unless otherwise specified. These drawings are not necessarily drawn to scale. It should be understood that these drawings depict only some embodiments according to the present disclosure herein and are not to be construed as limiting the scope of the present application.

DETAILED DESCRIPTION OF THE INVENTION

Only some exemplary embodiments are briefly described below. As can be appreciated by those skilled in the art, the described embodiments can be modified in various ways without departing from the spirit or scope of the present application. Accordingly, the drawings and the description are considered as illustrative in nature, and not as restrictive.

The present disclosure first provides a position adjustment apparatus 100 for adjusting a position of a detection device. The position adjustment apparatus 100 will be described in detail with reference to FIGS. 1 to 7.

Figure 1:
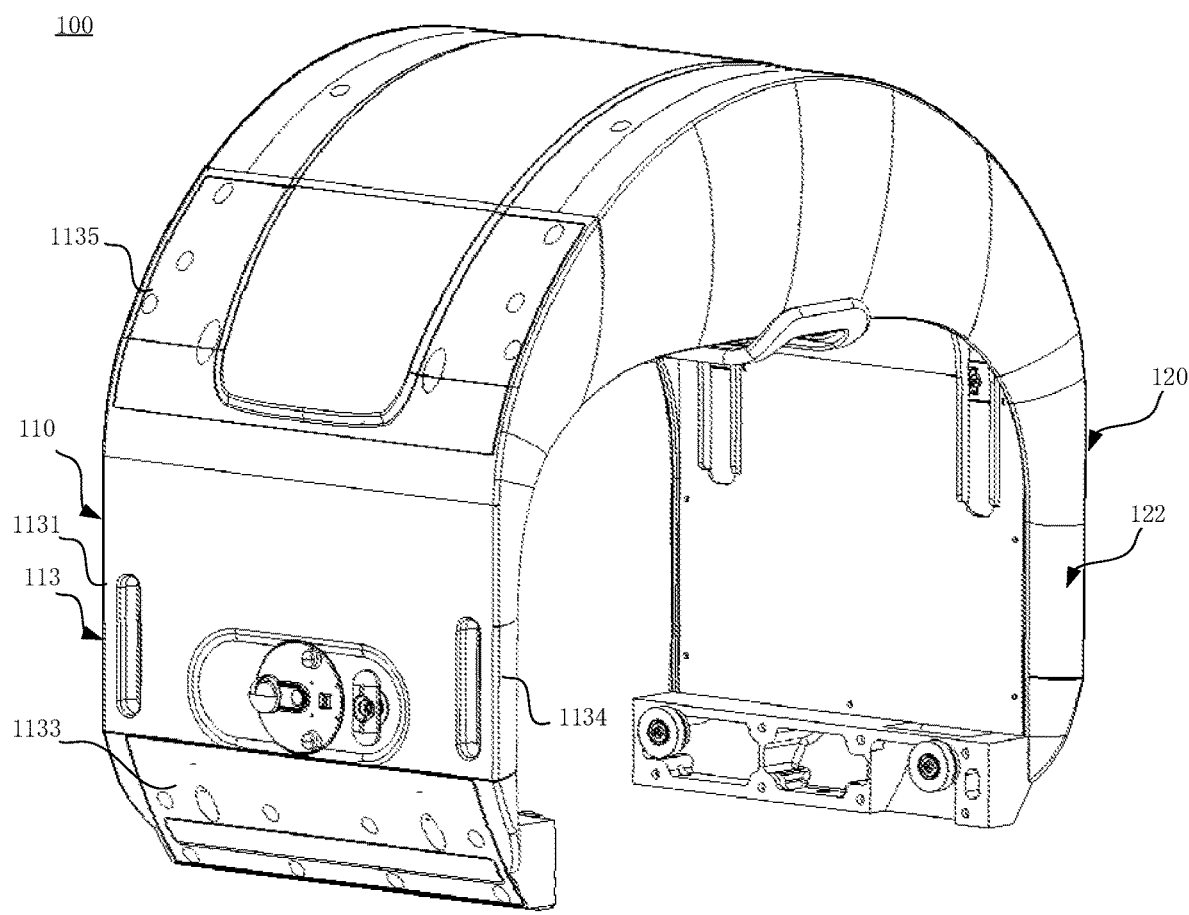
FIG. 1 shows a schematic view of the appearance of a position adjustment apparatus according to an embodiment of the present disclosure.
Figure 2:
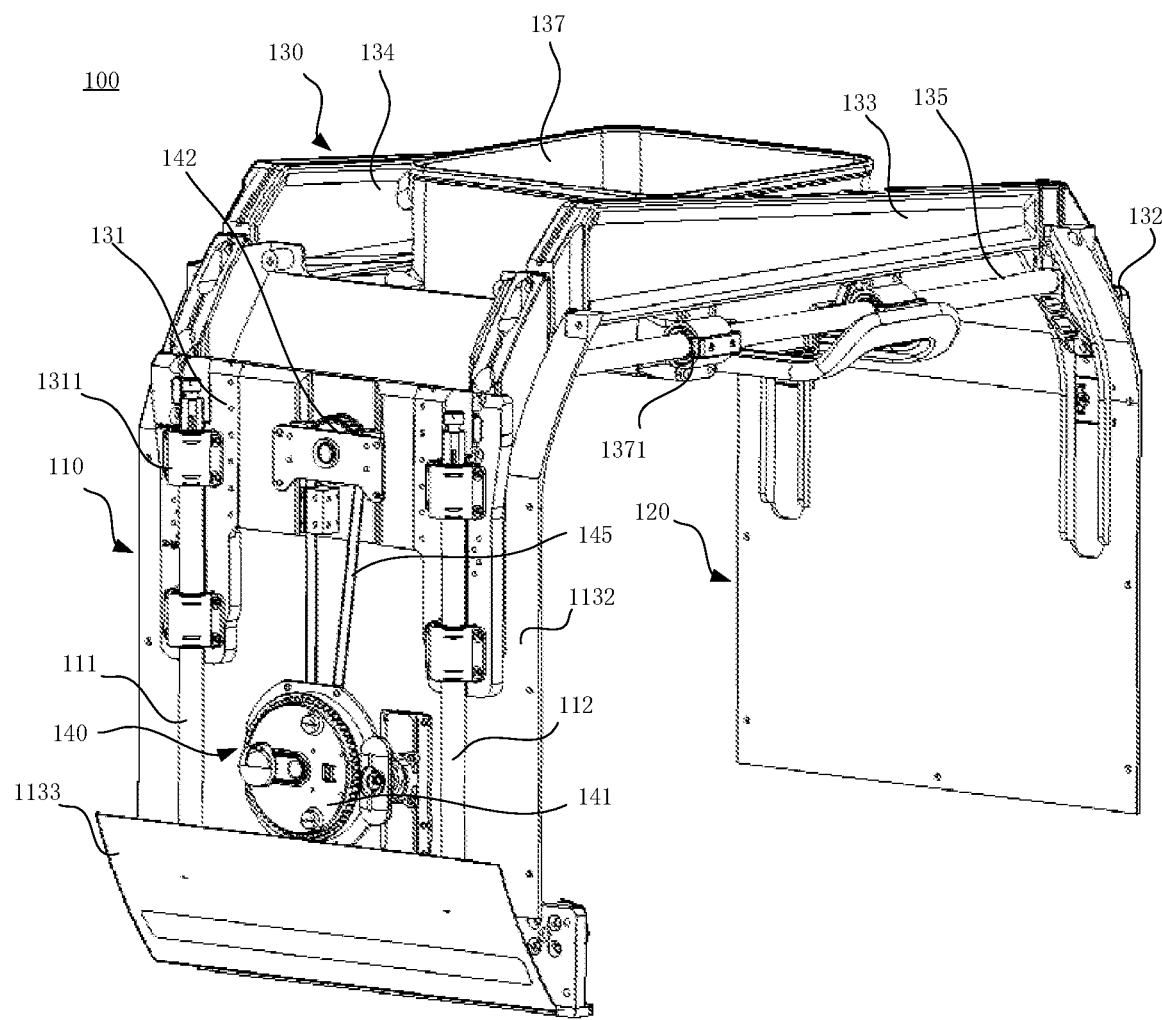
FIG. 2 shows a schematic view of a position adjustment apparatus with part of a housing removed according to an embodiment of the present disclosure.

FIG. 1 shows a schematic view of the appearance of a position adjustment apparatus 100 according to an embodiment of the present disclosure. FIG. 2 shows a schematic view of a position adjustment apparatus 100 with part of a housing removed according to an embodiment of the present disclosure. As shown in FIG. 2, the position adjustment apparatus 100 generally comprises: two support assemblies, a lifting frame 130 and at least one height adjustment assembly 140.

The two support assemblies are respectively arranged on the left and right sides of the lifting frame 130 and form a basic structure for supporting the lifting frame 130. Each support assembly comprises at least one support rod. The lifting frame 130 is arranged between the two support assemblies, the lifting frame has two ends respectively slidably connected to the support rods of the two support assemblies and is configured to move in a height direction of the support rods, and the lifting frame 130 comprises a mounting portion 137 for mounting the detection device. As shown in FIG. 2, the lifting frame 130 and the two support assemblies jointly form an arch structure. The at least one height adjustment assembly 140 is arranged on one side of at least one of the two support assemblies and is configured to adjust a lifting height of the lifting frame 130 to drive the detection device to move up and down in the mounting portion 137, so as to reach a detection height suitable for the detection device. Each height adjustment assembly 140 comprises: a first pulley 141 and a second pulley 142 arranged in the height direction of the support rods, and a drive belt 145. Rotating shafts of the first pulley 141 and the second pulley 142 are both fixedly arranged on the support assembly on the corresponding side. The drive belt 145 is wound around the first pulley 141 and the second pulley 142, the lifting frame 130 is fixedly connected to a predetermined position on the drive belt 145, and the drive belt 145 is configured to drive the lifting frame 130 to move as the first pulley 141 and the second pulley 142 rotate.

The position adjustment apparatus 100 of this embodiment enables free control over the height of the lifting frame 130 by providing the support rods and the height adjustment assembly 140 comprising a pulley block. A user can adjust the height of the detection device by manually rotating the first pulley 141 or the second pulley 142, and the operation is simple and convenient. In addition, no electrical devices such as an electric motor are provided inside the position adjustment apparatus 100 of this embodiment, and the adjustment of the position of the detection device is completely performed manually, so that it is especially suitable for a detection environment in which the electric devices are not suitable for use.

The support assemblies, the lifting frame 130, and the height adjustment assembly 140 will be described in detail below.

Figure 3:
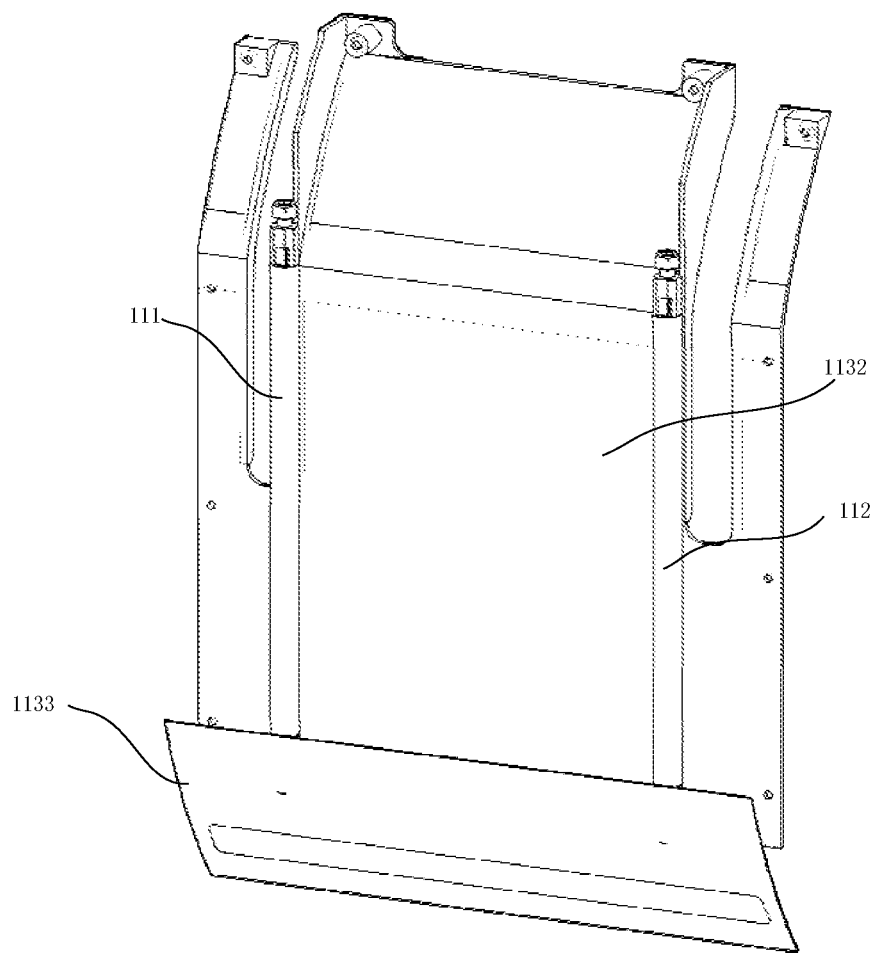
FIG. 3 shows a schematic view of a first support assembly of a position adjustment apparatus according to an embodiment of the present disclosure.
Figure 4:
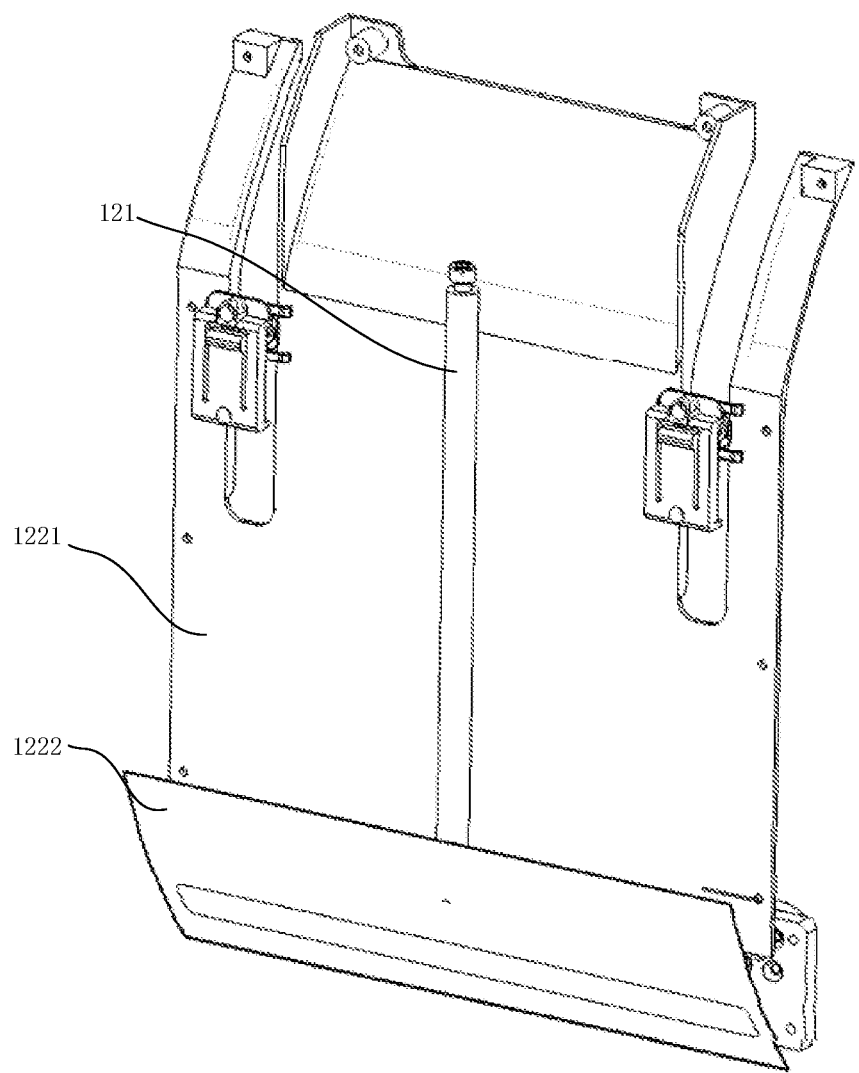
FIG. 4 shows a schematic view of a second support assembly of a position adjustment apparatus according to an embodiment of the present disclosure.

FIG. 3 shows a schematic view of a first support assembly 110 of a position adjustment apparatus 100 according to an embodiment of the present disclosure. FIG. 4 shows a schematic view of a second support assembly 120 of a position adjustment apparatus 100 according to an embodiment of the present disclosure. To better illustrate the two support assemblies described above, part of a housing of each support assembly is removed in FIGS. 3 and 4.

As shown in FIG. 3, the first support assembly 110 mainly comprises: a first support rod 111, a second support rod 112, and a first housing 113. The first support rod 111 and the second support rod 112 have the same height and are both vertically arranged. The height of the two support rods may be set according to actual detection requirements. The first housing 113 forms a chamber for accommodating the first support rod 111 and the second support rod 112. The first housing 113 mainly comprises: a first front plate 1131, a first back plate 1132, a first bottom plate 1133, a first top plate 1135, and two first side plates 1134 respectively forming left and right sides of the first support assembly 110, which are fixedly connected to one another (in FIG. 3, the first front plate 1131, the first top plate 1135 and the two first side plates 1134 are removed, and are therefore are shown). The first support rod 111 and the second support rod 112 are respectively arranged on the left and right sides of the chamber space formed by the first housing 113 to give more balanced supporting to the lifting frame 130, and the first support rod 111 and the second support rod 112 may also be spaced apart by a certain distance to provide a mounting space of the height adjustment assembly 140, which will be described in detail later. In this embodiment, bottom ends of the first support rod 111 and the second support rod 112 may be fixed to the first bottom plate 1133 to realize the fixed connection between the two support rods and the first housing 113. In some other embodiments of the present disclosure, the first support rod 111 and the second support rod 112 may alternatively be fixed to the first back plate 1132, the first top plate 1135, or the first front plate 1131. It will be appreciated that in some other embodiments of the present disclosure, the first support assembly 110 may alternatively be provided with more than two support rods, such as three or five support rods. In any case, the solution of the present disclosure is not limited by the number of support rods.

As shown in FIG. 4, the second support assembly 120 mainly comprises: a third support rod 121 and a second housing 122. The third support rod 121 has the same height as the first support rod 111 and the second support rod 112 and is vertically arranged. The second housing 122 forms a chamber for accommodating the third support rod 121. The second housing 122 mainly comprises: a second front plate, a second back plate 1221, a second bottom plate 1222, a second top plate, and two second side plates respectively forming left and right sides of the second support assembly 120, which are fixedly connected to one another (in FIG. 4, the second front plate, the second top plate and the two second side plates are removed). The third support rod 121 may be arranged in the center of the chamber space formed by the second housing 122, to give more balanced supporting to the lifting frame 130. In this embodiment, the third support rod 121 may be fixed to the second bottom plate 1222 to realize the fixed connection between the third support rod 121 and the second housing 122. In some other embodiments of the present disclosure, the third support rod 121 may alternatively be fixed to the second back plate, the second top plate, or the second front plate. It will be appreciated that in some other embodiments of the present disclosure, the second support assembly 120 may also be provided with two or more support rods.

Figure 5:
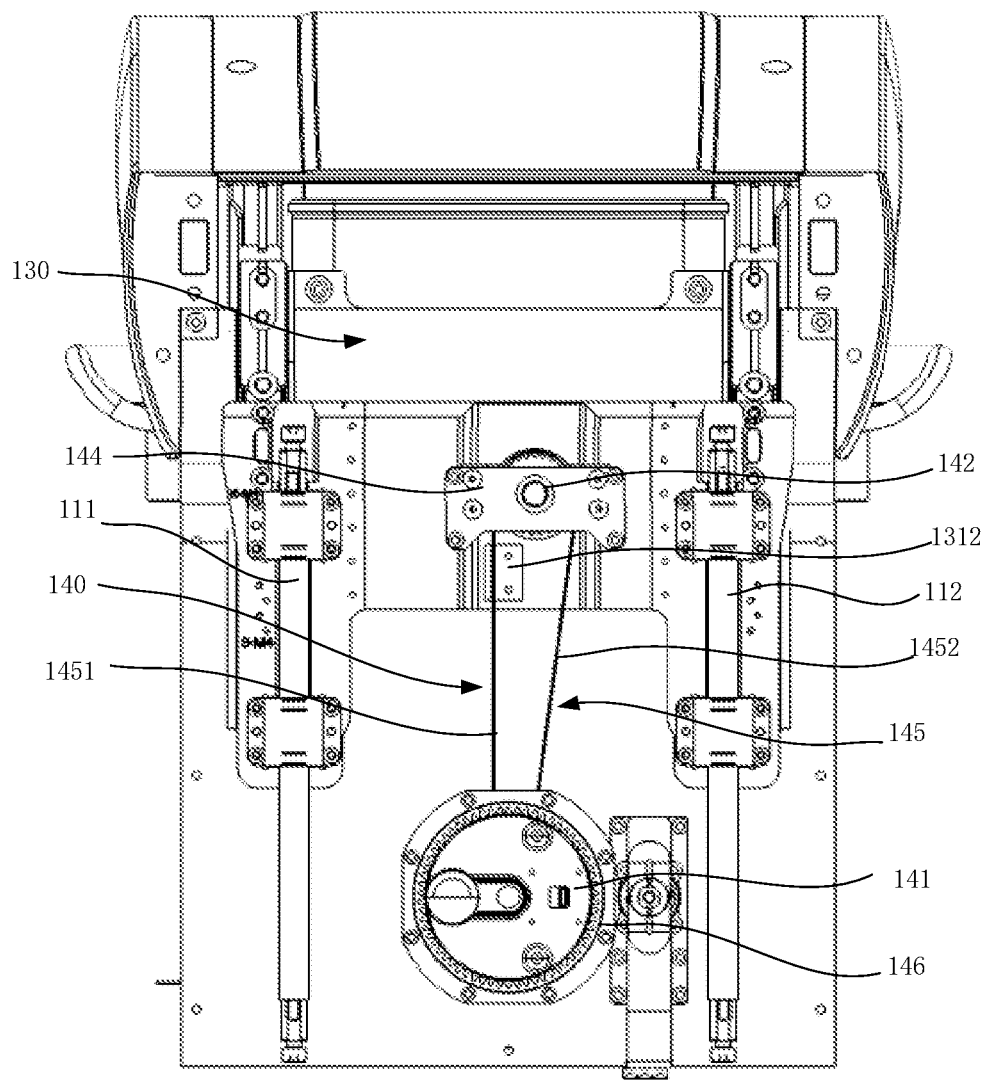
FIG. 5 shows a side view of one side of a first support assembly of a position adjustment apparatus according to an embodiment of the present disclosure.

FIG. 5 shows a side view of one side of a first support assembly 110 of a position adjustment apparatus 100 according to an embodiment of the present disclosure. As shown in FIG. 5, in this embodiment, the position adjustment apparatus 100 comprises only one height adjustment assembly 140, and the height adjustment assembly 140 is arranged on one side of the first support assembly 110. The height adjustment assembly 140 is arranged inside the first housing 113 and is arranged between the first support rod 111 and the second support rod 112. Preferably, the distances from the height adjustment assembly 140 to the first support rod 111 and the second support rod 112 are the same, such that the height adjustment assembly 140 can drive the lifting frame 130 to move up and down in a relatively balanced manner, preventing the lifting frame 130 from tilting toward one side during movement. Although the position adjustment apparatus 100 having only one height adjustment assembly 140 is shown in this embodiment, it may be understood that in some other embodiments of the present disclosure, the position adjustment apparatus 100 may alternatively comprise two or more height adjustment assemblies 140, and a plurality of height adjustment assemblies 140 may be arranged on either or both sides of the first support assembly 110 or the second support assembly 120.

Each height adjustment assembly 140 comprises: a first pulley 141, a second pulley 142 and a drive belt 145. The first pulley 141 and the second pulley 142 are arranged in the height direction of the support rods. For example, the first pulley 141 is arranged at a lower position, and the second pulley 142 is arranged above the first pulley 141. In addition, the fixing positions of the first pulley 141 and the second pulley 142 are required to ensure that the part of the drive belt 145 fixedly connected to the lifting frame 130 is vertically arranged. As shown in FIG. 5, the drive belt 145 may comprise a first part 1451 and a second part 1452, wherein the first part 1451 is vertically arranged and fixedly connected to the lifting frame 130, which will be described in detail below. The rotating shaft of the first pulley 141 may be fixed to the first back plate 1132 by means of a first fixing member 143 (not shown due to being hidden), while the rotating shaft of the second pulley 142 may be fixed to the first front plate 1131 by means of a second fixing member 144 (in FIG. 5, the second fixing member 144 seems to be separated from the first front plate 1131 because the first front plate 1131 is removed, but in an actual structure, the second fixing member 144 is fixedly arranged on the first front plate 1131). Therefore, the rotating shafts of the first pulley 141 and the second pulley 142 are both fixed to the first housing 113, and the relative position between the two pulleys is fixed. The first fixing member 143 and the second fixing member 144 may both be fixed to the respective positions of the first housing 113 by screwing or other means, and the structure and arrangement of such fixing members are well known to those skilled in the art and will not be described in detail herein.

Figure 6:
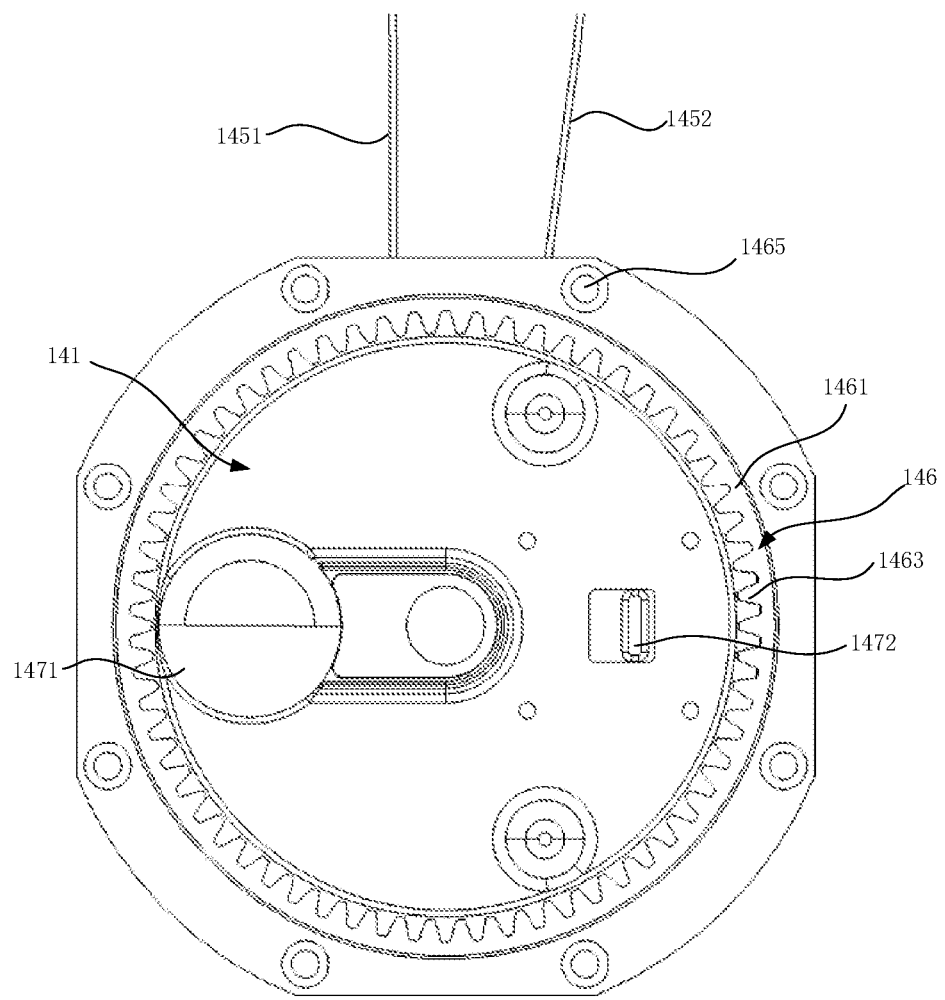
FIG. 6 shows a side view of a first pulley and a locking mechanism in a height adjustment assembly of a position adjustment apparatus according to an embodiment of the present disclosure.
Figure 7:
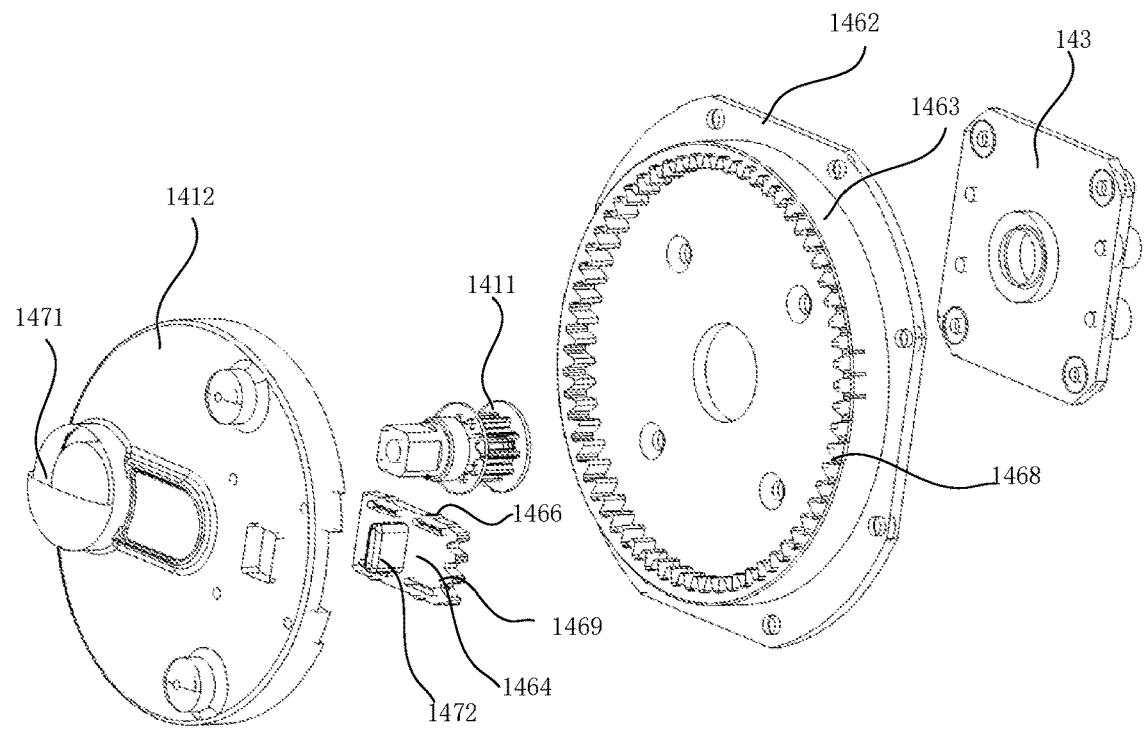
FIG. 7 shows a structural exploded view of the first pulley and the locking mechanism shown in FIG. 6.
Figure 8:
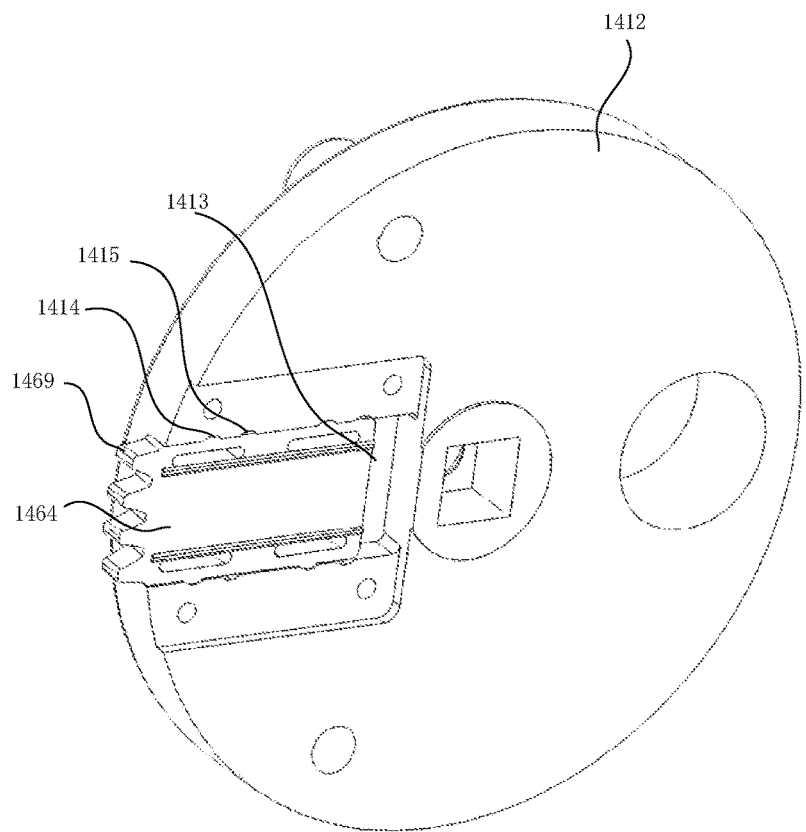
FIG. 8 shows a schematic view of an outer rotating disk of the first pulley shown in FIG. 6.

The first pulley 141 and a locking mechanism 146 for locking the first pulley 141 will be described in detail below. FIG. 6 shows a side view of the first pulley 141 and the locking mechanism 146 in a height adjustment assembly 140 of a position adjustment apparatus 100 according to an embodiment of the present disclosure. FIG. 7 shows a structural exploded view of the first pulley 141 and the locking mechanism 146 shown in FIG. 6. FIG. 8 shows a schematic view of an outer rotating disk 1412 of the first pulley 141 shown in FIG. 6.

As shown in FIGS. 6 and 7, the first pulley 141 comprises: an inner wheel 1411 and an outer rotating disk 1412 that are coaxial with each other, the inner wheel 1411 and the outer rotating disk 1412 may be connected by means of a shaft connecting portion. Specifically, the shaft connecting portion laterally protrudes from a rotating shaft of the inner wheel 1411, and has a square end face at the protruding end. A square groove is correspondingly formed at the center of the back side of the outer rotating disk 1412, and the inner wheel 1411 can be coaxially connected to the outer rotating disk 1412 by inserting the protruding end of the shaft connecting portion into the groove. The inner wheel 1411 is located on the side close to the first back plate 1132 relative to the outer rotating disk 1412.

The locking mechanism 146 comprises: a fixed toothed disk 1461 and a limiting push piece 1464. The fixed toothed disk 1461 is fixedly arranged on the support assembly on the corresponding side, wherein a hollow portion for accommodating at least a part of the first pulley 141 is provided in the center of the fixed toothed disk, and a plurality of limiting teeth 1468 are arranged on an inside periphery of the hollow portion. Specifically, as shown in FIG. 7, the fixed toothed disk 1461 may be fixed to the first back plate 1132 of the first housing 113 by means of a toothed disk fixing member 1465, and the above-described fixed connection may be realized, for example, by screwing. The fixed toothed disk 1461 comprises a base plate 1462 and a ring gear 1463 fixedly arranged on the base plate 1462, and the base plate 1462 and the ring gear 1463 jointly define the hollow portion. The diameter of the ring gear 1463 may be greater than that of the outer rotating disk 1412 such that the outer rotating disk 1412 can be accommodated within the hollow portion. The base plate 1462 may be provided with a through hole at the center to allow the inner wheel 1411 to extend out of the base plate 1462. That is, the outer rotating disk 1412 and the inner wheel 1411 are respectively arranged on two sides of the base plate 1462. The inner wheel 1411 is located directly below the second pulley 142, and the drive belt 145 is wound around the inner wheel 1411 and the second pulley 142. The limiting push piece 1464 is slidably arranged on the first pulley 141 and configured to slide in a radial direction of the first pulley 141, and the end of the limiting push piece 1464 facing the inside periphery of the hollow portion is further provided with complementary teeth 1469 that are complementary with the plurality of limiting teeth 1468. Specifically, as shown in FIG. 8, the limiting push piece 1464 is arranged on the outer rotating disk 1412. FIG. 8 shows the side of the outer rotating disk 1412 facing the fixed toothed disk 1461, this side of the outer rotating disk 1412 is provided with a guide groove 1413 for accommodating the limiting push piece 1464, and the guide groove 1413 extends in the radial direction of the outer rotating disk 1412 and allows the limiting push piece 1464 to slide in the radial direction of the outer rotating disk 1412.

A plurality of limiting protrusions 1466 and limiting recesses cooperating with each other are provided at corresponding positions of two side edges of the limiting push piece 1464 and an inner side of the guide groove 1413, and the limiting push piece 1464 has a first position and a second position that are defined jointly by the limiting protrusions 1466 and the limiting recesses. For example, four limiting protrusions 1466 are arranged on the two side edges of the limiting push piece 1464, and two sets of limiting recesses each including four limiting recesses are arranged on the inner side of the guide groove 1413. The two sets of limiting recesses comprise: a first set of limiting recesses 1414 and a second set of limiting recesses 1415. When the limiting push piece 1464 is pushed outwardly in the radial direction of the outer rotating disk 1412, the four limiting protrusions 1466 thereof are engaged with the first set of limiting recesses 1414, and the limiting push piece 1464 is in the first position. When the limiting push piece 1464 is pushed inwardly in the radial direction of the outer rotating disk 1412, the four limiting protrusions 1466 thereof are engaged with the second set of limiting recesses 1415, and the limiting push piece 1464 is in the second position. The locking mechanism 146 is configured such that when the limiting push piece 1464 is pushed into the first position, the complementary teeth 1469 are meshed with at least some of the plurality of limiting teeth 1468 to lock the first pulley 141. When the limiting push piece 1464 is pushed into the second position, the complementary teeth 1469 are separated from the plurality of limiting teeth 1468 to release the first pulley 141. The limiting push piece 1464 is further provided with a shank 1472, the shank 1472 extends out through a hole pre-formed in the outer rotating disk 1412 to facilitate pushing of the limiting push piece 1464 by the user.

As shown in FIG. 1, the part of the first housing 113 corresponding to the outer rotating disk 1412 is provided with an opening for exposing at least a part of the outer rotating disk 1412 outside the housing. Specifically, the first front plate 1131 of the first housing 113 is provided with a circular opening sized to match the outer rotating disk 1412, the circular opening allows the side of the outer rotating disk 1412 facing away from the fixed toothed disk 1461 to be exposed, so as to facilitate performing turning operation on the outer rotating disk by the user. In addition, the outer rotating disk 1412 further comprises: a handle 1471 arranged on the part of the outer rotating disk 1412 exposed outside the housing to facilitate rotating the outer rotating disk 1412 by the user. In addition, the shank 1472 is also arranged on the part of the outer rotating disk 1412 exposed outside the housing to facilitate the operation by the user.

The use principle of the position adjustment apparatus 100 of this embodiment is as follows: when the user desires to adjust the detection height of the detection device, the outer rotating disk 1412 may be manually rotated from the outer side, the limiting push piece 1464 is now in the second position, and the outer rotating disk 1412 can freely rotate. When the outer rotating disk 1412 is rotated clockwise, the pulley block will drive the first part 1451 of the drive belt 145 to move upwards, thereby driving the lifting frame 130 to ascend by means of an engagement portion 1312, and increasing the height of the detection device. When the outer rotating disk 1412 is rotated counterclockwise, the pulley block will drive the first part 1451 of the drive belt 145 to move downwards, thereby driving the lifting frame 130 to descend by means of the engagement portion 1312, and decreasing the height of the detection device. When the detection device is adjusted to a desired height, the limiting push piece 1464 is pushed into the first position, and the complementary teeth 1469 are meshed with at least some of the plurality of limiting teeth 1468, the rotation of the first pulley 141 is now locked, and the position and height of the detection device is fixed at the same time. In addition, since the limiting teeth 1468 are arranged on the inside periphery of the hollow portion of the fixed toothed disk 1461, regardless of what angle the limiting push piece 1464 is rotated, when the limiting push piece 1464 is pushed into the first position, the complementary teeth 1469 thereof can be meshed with the corresponding some of the limiting teeth 1468, thereby achieving the purpose of locking.

The position adjustment apparatus 100 of this embodiment can realize height adjustment and positioning of the detection device by means of the cooperation between the pulley block and the locking mechanism 146. The limiting push piece 1464 for locking purpose is arranged on the outer rotating disk 1412, so that the user can conveniently and quickly lock the first pulley 141 after rotating the outer rotating disk 1412, greatly improving the practicality of the position adjustment apparatus 100. In addition, the provision of the structure in which the outer rotating disk 1412 is exposed from the first front plate 1131 enables the user to control the height of the detection device from the side of the position adjustment apparatus 100 without the need for inserting a hand into the housing of the position adjustment apparatus 100 or between the two support assemblies, thereby further simplifying the operation.

Figure 9:
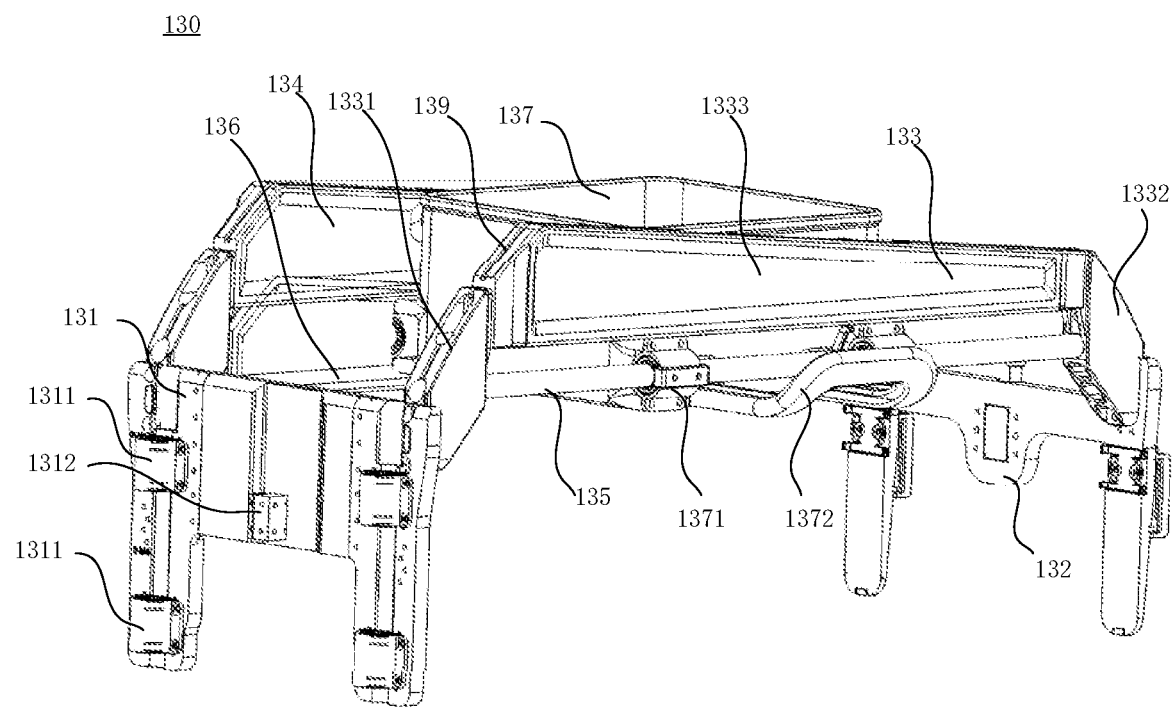
FIG. 9 shows a schematic view of a lifting frame of a position adjustment apparatus according to an embodiment of the present disclosure.

FIG. 9 shows a schematic view of a lifting frame 130 according to an embodiment of the present disclosure. As shown in FIG. 9, the lifting frame 130 mainly comprises: a first end plate 131, a second end plate 132, a first cross beam 133, a second cross beam 134, a first sliding rod 135, a second sliding rod 136, and a mounting portion 137. The first end plate 131 is slidably connected to the support rods of the first support assembly 110, namely, the first support rod 111 and the second support rod 112. The second end plate 132 is slidably connected to the support rod of the second support assembly 120, namely, the third support rod 121. Two ends of each cross beam are respectively connected to the first end plate 131 and the second end plate 132. The first end plate 131 is fixedly provided with two sets of sleeves at the positions corresponding to the two support rods, and the sleeves of each set are respectively fitted outside the corresponding support rods. In this embodiment, the two sets of sleeves are respectively arranged in the regions of the first end plate 131 close to the left and right side edges thereof so as to respectively correspond to the positions of the first support rod 111 and the second support rod 112, and each set of sleeves comprises two sleeves 1311 arranged in the height direction of the support rods. The second end plate 132 is fixedly provided with a set of sleeves at the position corresponding to the support rod, and the sleeves are fitted outside the support rod. In this embodiment, the set of sleeves is arranged in the center of the second end plate 132 to correspond to the position of the third support rod 121. In addition, a damping layer is further provided between the sleeve 1311 and the corresponding support rod. The damping layer may be fixedly arranged on an inner wall of the sleeve 1311, and the damping layer may be made of a material with a high coefficient of friction, such as rubber and foam plastic. The first end plate 131 is further provided with the engagement portion 1312 for fixedly connecting the drive belt 145, and the engagement portion 1312 may be a bump fixed to the first end plate 131. The engagement portion 1312 is provided with a slit allowing the drive belt 145 to pass through, and the engagement portion 1312 is fixed to a predetermined position of the drive belt 145 by means of a screw transversing the slit.

In this embodiment, it is possible to freely move the lifting frame 130 in the height direction of the support rod by means of the mutual cooperation of the sleeve 1311 and the support rod. The damping layer generates a resistance to the relative movement between the sleeve 1311 and the support rod, allowing the relative movement therebetween to be smoother. Although the relative sliding between the support rods and the lifting frame 130 is realized by means of the sleeves 1311 in this embodiment, it will be appreciated that in some other embodiments of the present disclosure, the sliding connection between the lifting frame 130 and the support rods may alternatively be realized by other means. For example, the first end plate 131 and the second end plate 132 may be provided with recessed sliding tracks, and the relative sliding between the support rods and the lifting frame 130 is realized by placing the support rods in the sliding tracks.

At least a part of an upper surface of the cross beam is arranged tilted downwards in a direction from the first end plate 131 to the second end plate 132. Since the height adjustment assembly 140 is arranged on the first support assembly 110 side (hereinafter referred to as first side) in this embodiment, the first side is a side where a force is actively applied, and the second support assembly 120 side (hereinafter referred to as second side) is a side that is passively stressed. The inventors have found after a number of experiments that, in the case where the upper surface of the cross beam is made completely horizontal, the lifting speed of the part of the cross beam close to the first side is slightly higher than that of the part close to the second side, and the overall movement of the lifting frame 130 may thus be imbalanced. In order to solve the above-mentioned problem, the inventors have consciously configured the upper surface of the cross beam in the form of a structure tilted downwards in the direction from the first end plate 131 to the second end plate 132, thereby balancing the lifting speeds of two ends of the cross beam, and in turn ensuring that the lifting frame 130 moves more smoothly.

Specifically, as shown in FIG. 9, taking the first cross beam 133 as an example, the first cross beam 133 has a three-section structure, comprising: a first connecting section 1331, a second connecting section 1332 and a transversely extending section 1333. One end of the first connecting section 1331 is connected to the first end plate 131, one end of the second connecting section 1332 is connected to the second end plate 132, and two ends of the transversely extending section 1333 are respectively connected to the first connecting section 1331 and the second connecting section 1332. An upper surface of the first connecting section 1331 extends obliquely upwards from the first end plate 131, an upper surface of the transversely extending section 1333 extends obliquely downwards from an end of the first connecting section 1331, an upper surface of the second connecting section 1332 extends obliquely downwards from an end of the transversely extending section 1333, and the degree of tilting of the upper surface of the second connecting section 1332 is greater than that of the upper surface of the transversely extending section 1333. Such an arrangement allows the upper surface of the first cross beam 133 to have a highest point.

Figure 10:
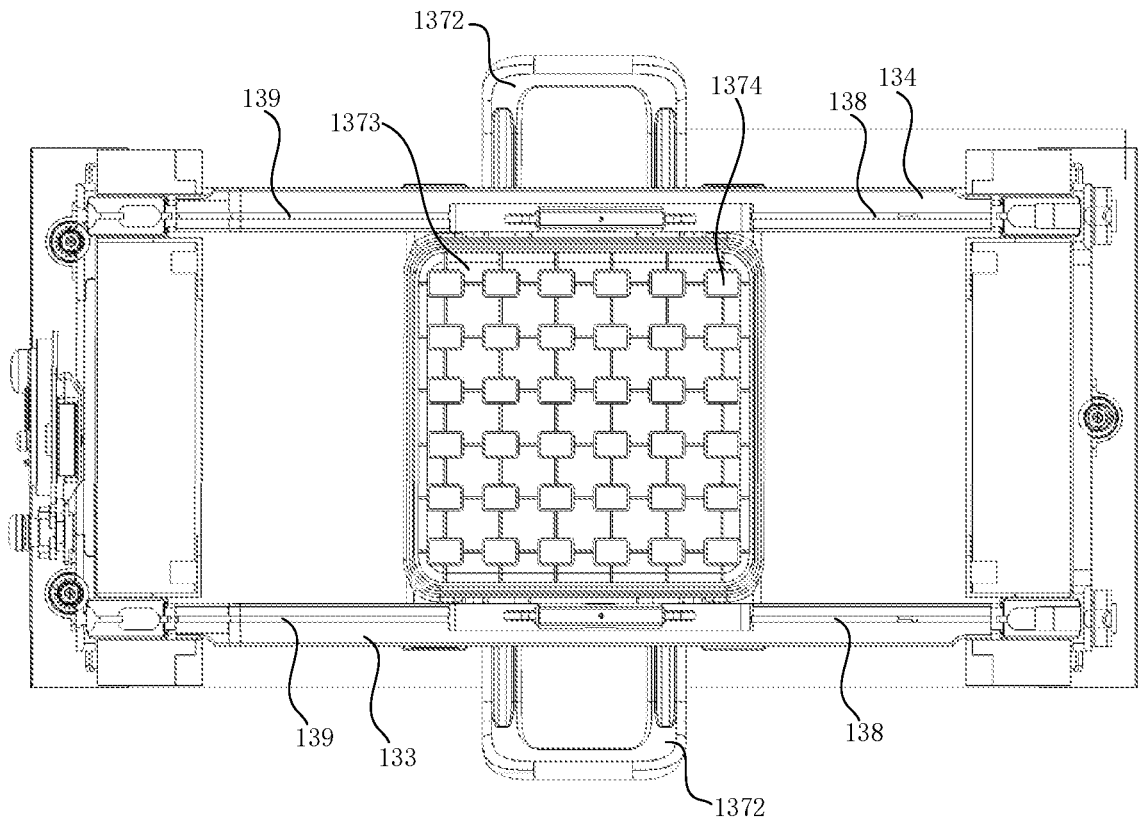
FIG. 10 shows a top view of a position adjustment apparatus according to an embodiment of the present disclosure.

The lifting frame 130 further comprises: at least one structural reinforcing rope 138. Two ends of each structural reinforcing rope 138 are respectively connected to two ends of one cross beam. As shown in FIG. 9, the upper surface of the cross beam is further provided with a wire guide groove 139 for accommodating the structural reinforcing rope 138. FIG. 10 shows a top view of a position adjustment apparatus 100 according to an embodiment of the present disclosure. In FIG. 10, part of the housing at the top of the position adjustment apparatus 100 is removed for a clear view of the internal structure thereof. The wire guide groove 139 can be more clearly seen from FIG. 10. Specifically, the two ends of the structural reinforcing rope 138 are respectively fixedly connected to the first connecting section 1331 and the second connecting section 1332, and the first connecting section 1331 and the second connecting section 1332 are provided with fixing holes for respectively fixing the two ends of the structural reinforcing rope 138. A fastening screw is provided in each fixing hole, and one end of the structural reinforcing rope 138 may be wound around the fastening screw to realize the connection with the first connecting section 1331 or the second connecting section 1332. The structural reinforcing rope 138 of this embodiment may be a nonmetallic rope such as a nylon rope and a plastic rope.

The structural reinforcing rope 138 of this embodiment enhances the overall structural stability of the lifting frame 130. In addition, the structural reinforcing rope 138 connects the two ends of the cross beam and also passes the highest point of the upper surface of the cross beam, and the above-mentioned arrangement forms a suspension bridge-like structure. Such a structure enables the two ends of the crossbeam to be uniformly stressed, thereby making the movement speeds at the two ends of the cross beam the same, and ensuring a more stable movement of the lifting frame 130.

The lifting frame 130 further comprises: at least two sliding rods arranged in parallel. Two ends of each sliding rod are respectively directly or indirectly connected to the first end plate 131 and the second end plate 132. The mounting portion 137 further comprises a plurality of sleeves 1371. The plurality of sleeves 1371 are fitted on the at least two sliding rods such that the mounting portion 137 slides along the sliding rods. Specifically, as shown in FIGS. 9 and 10, the lifting frame 130 comprises the first sliding rod 135 and the second sliding rod 136, the first sliding rod 135 is arranged directly below the first crossbeam 133, and the second sliding rod 136 is arranged directly below the second crossbeam 134. Taking the first sliding rod 135 as an example, two ends of the first sliding rod 135 are respectively fixed to the first connecting section 1331 and the second connecting section 1332. That is to say, the first sliding rod 135 is indirectly connected to the first end plate 131 and the second end plate 132 respectively by means of the first connecting section 1331 and the second connecting section 1332. The mounting portion 137 may be a rectangular box and is arranged between the two sliding rods, and the side of the mounting portion facing the first sliding rod 135 and the side thereof facing the second sliding rod 136 are both provided with two sleeves 1371 for fitting on the corresponding sliding rods. The mounting portion 137 further comprises an armrest 1372 to facilitate pushing the mounting portion 137 to slide. As shown in FIG. 9, the armrest 1372 may be arranged between the two sleeves 1371. A damping layer may also be provided between the sleeve 1371 and the sliding rod to make the relative movement between the sleeve 1371 and the sliding rod more stable.

In the position adjustment apparatus 100 of this embodiment, the mounting portion 137 thereof may slide in the length direction of the sliding rods, so that the transverse position of the detection device can be adjusted, and in combination with the application of the height adjustment assembly 140, two-dimensional adjustment of the position of the detection device can be further realized.

The detection device may be a device specially used for detecting a magnetic field of the human body. The detection device comprises a plurality of magnetometer probes, which are means for detecting magnetic fields. The mounting portion 137 further comprises a mounting panel 1373, and the mounting panel 1373 is provided with a plurality of slotted holes for having the plurality of magnetometer probes 1374 placed therein. As shown in FIG. 10, the mounting panel 1373 is placed flat at the bottom of the mounting portion 137. The mounting panel 1373 is provided with a plurality of slotted holes 1374, and the slotted holes 1374 may be arranged in an M×N array. After the plurality of magnetometer probes are respectively placed in the slotted holes 1374, an M×N array of detection probes is formed, which can be used for detecting a magnetic field of a target at multiple points.

The position adjustment apparatus 100 is integrally made of a nonmetallic material. The above-mentioned nonmetallic material may be a high-molecular polymer such as a resin, or a ceramic material. As described above, the position adjustment apparatus 100 of this embodiment may be specially used for the adjustment of the position of the detection device for detecting a magnetic field. Therefore, each of the components (including a screw for connection, etc.) of the position adjustment apparatus 100 is preferably made of the nonmetallic material, thereby preventing metal components in the position adjustment apparatus 100 from generating a magnetic field to interfere with the detection of the detection device. In addition, the position adjustment apparatus 100 is further integrally provided with a housing forming the appearance thereof, and the housing may comprise the first housing 113 and the second housing 122. The specific structure of the housing is a conventional arrangement in the art, which will not be described in detail herein.

According to another aspect of the present disclosure, further provided is a magnetocardiography instrument 1. The magnetocardiography instrument 1 is a completely non-invasive and high-sensitivity medical instrument with a magnetic field detection device placed over the heart to passively receive magnetic field signals generated by the electrophysiological activity of the heart. The magnetocardiography instrument 1 does not generate radioactive rays, does not form an external magnetic field, and does not use a developer, and the detection device does not come into contact with a patient. The magnetocardiography instrument 1 is typically placed in a separate room of 10-20 square meters and it is necessary to ensure that there is no strong magnetic field interference beyond 5 meters. The person to be detected does not need to make any preparation, and only needs to lie supine on the magnetocardiography instrument 1 for 1-10 minutes during scanning. The detection personnel can independently complete the detection process in a short time, and a detection result will be automatically recorded in a corresponding storage device. A magnetocardiogram generated by the magnetocardiography instrument 1 may be used for diagnosing whether the patient is suffering from problems such as myocardial ischemia, microangiopathy or ventricular hypertrophy. The magnetocardiography instrument 1 has a very high sensitivity and can accurately detect the traces of myocardial cell apoptosis or necrosis caused by previous myocardial ischemia.

Figure 11:
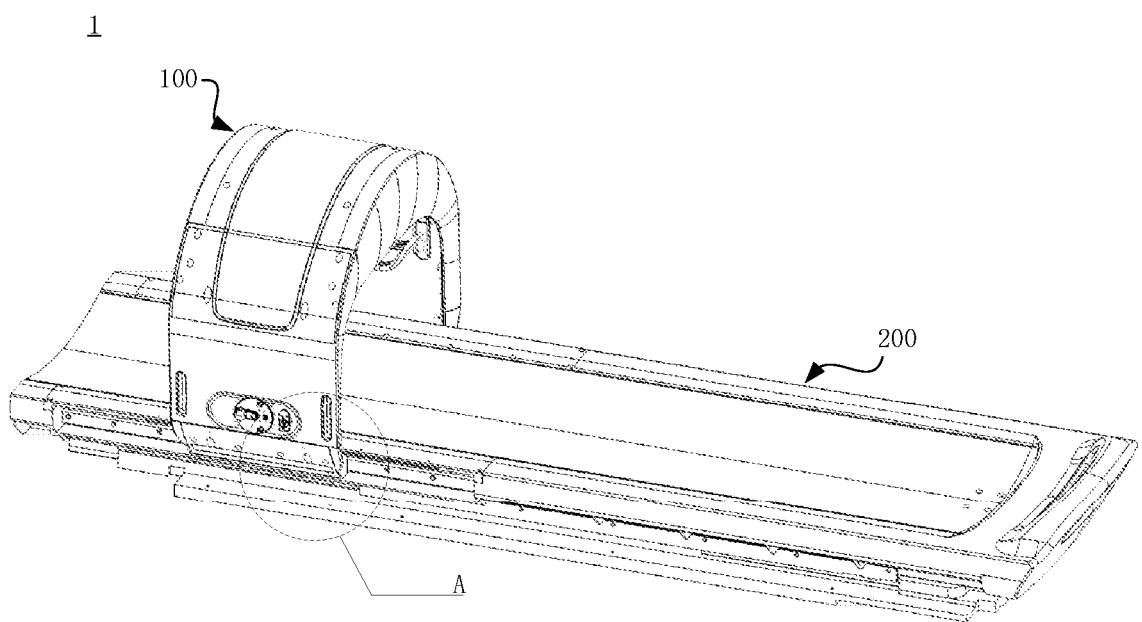
FIG. 11 shows a schematic view of a magnetocardiography instrument according to an embodiment of the present disclosure.

The magnetocardiography instrument 1 comprises: a bed body 200, the position adjustment apparatus 100 and a plurality of magnetometer probes. FIG. 11 shows a schematic view of a magnetocardiography instrument 1 according to an embodiment of the present disclosure. As shown in FIG. 11, the bed body 200 is substantially of a rectangular plate-like structure, and the person to be detected may lie on the bed body 200 to wait for examination. The bottom ends of the two support assemblies of the position adjustment apparatus 100 are respectively slidably connected to two side edges in a length direction of the bed body 200 such that the position adjustment apparatus 100 slides in the length direction of the bed body 200. The mounting of the plurality of magnetometer probes is described in detail above and will not be further described herein. Since the positions of the hearts of different individuals to be detected are different, the magnetocardiography instrument 1 needs to use the position adjustment apparatus 100 to adjust the position of the detection device so as to find an optimal position for detecting the magnetic field of the human heart.

Figure 12:
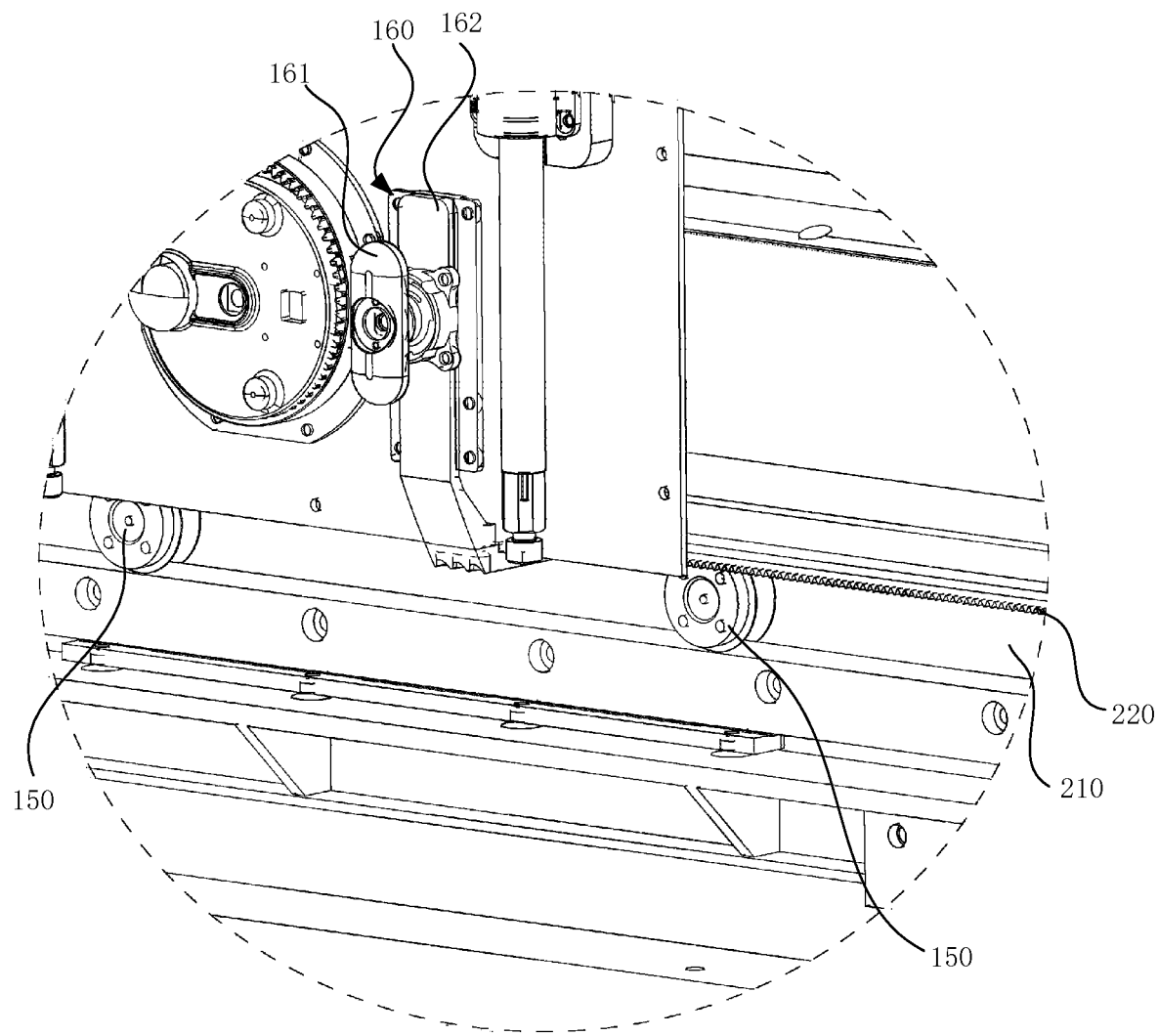
FIG. 12 shows a partially enlarged view of an area A in FIG. 11.

FIG. 12 shows a partially enlarged view of an area A in FIG. 11. As shown in FIG. 12, the bottom ends of the two support assemblies are further provided with a plurality of rollers 150. The bed body 200 is further provided with tracks 210 at the positions corresponding to the bottom ends of the two support assemblies, the tracks extending in the length direction of the bed body 200 for accommodating the plurality of rollers 150. The tracks 210 may be arranged on the left and right sides of the bed body 200. The plurality of rollers 150 are arranged on the sides of the bottom ends of the support assemblies facing the bed body 200 so as to be opposite the tracks 210. As shown in FIGS. 11 and 12, the width of the position adjustment apparatus 100 (the distance between the first support assembly 110 and the second support assembly 120) is slightly greater than that of the bed body 200, and the bottom ends of the two support assemblies are not directly above the two side edges of the bed body 200, but slightly beyond the width extent of the bed body 200 on two sides. The rollers 150 may be arranged on the inner sides of the bottom ends of the support assemblies, and correspondingly, the tracks 210 are arranged on the left and right sides of the bed body 200. Such an arrangement allows the rollers 150 and the tracks 210 not to occupy the upper surface of the bed body 200 and prevents same from coming into contact with the person to be detected during movement of the position adjustment apparatus 100. Since the detection device only detects the magnetic field around the heart of the human body, it is not necessary for the length of the tracks 210 to be equal to the length of the bed body 200. For example, the length of the tracks 210 may be only half of the length of the bed body 200.

Figure 13:
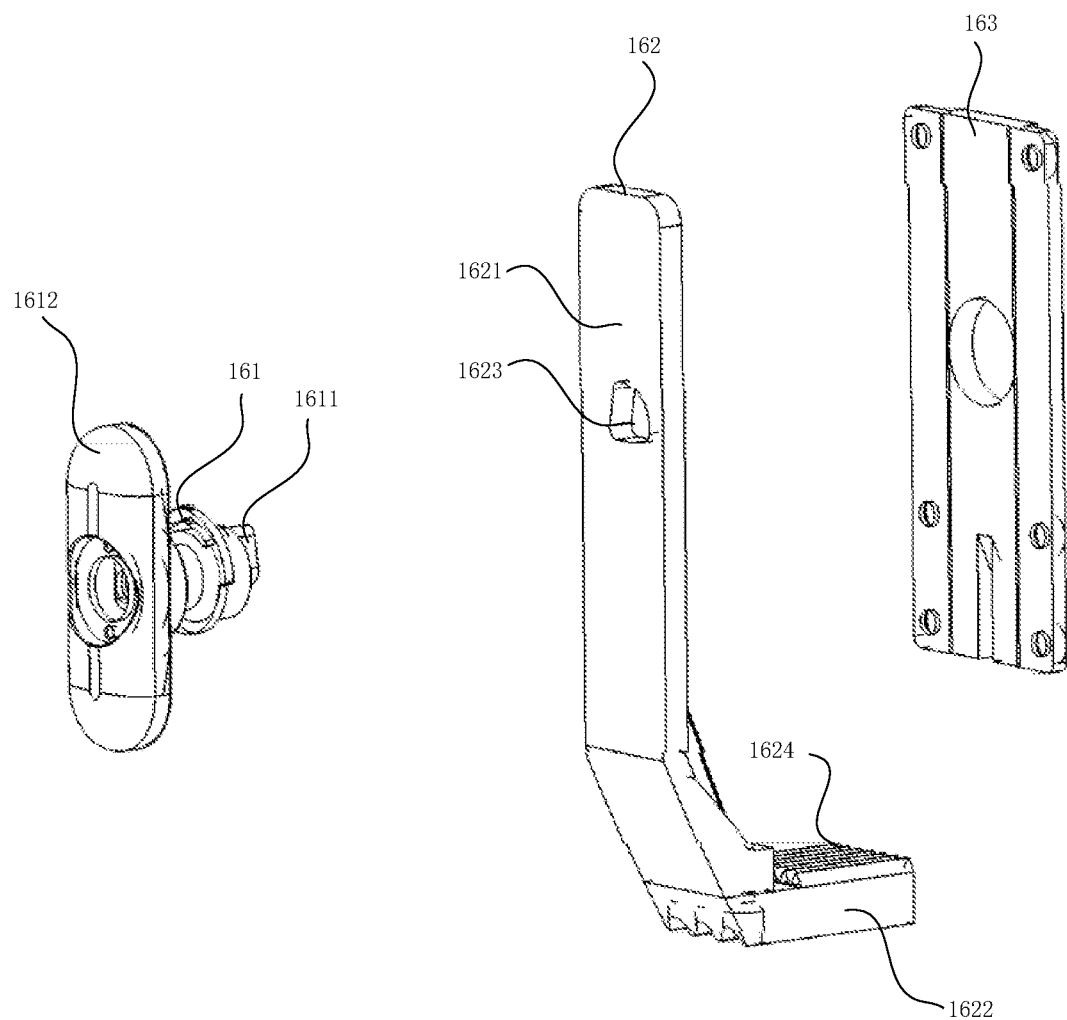
FIG. 13 shows a structural exploded view of a limiting mechanism of a magnetocardiography instrument according to an embodiment of the present disclosure.

The bed body 200 is further provided with a rack 220 extending in the length direction thereof, and the position adjustment apparatus 100 further comprises a limiting mechanism 160. The limiting mechanism 160 comprises: a cam-knob 161 and a limiting member 162. FIG. 13 shows an exploded view of a limiting mechanism 160 of a magnetocardiography instrument 1 according to an embodiment of the present disclosure. As shown in FIGS. 11 and 12, in order to save space, the rack 220 may be arranged on an upper surface of the track 210. The cam-knob 161 is rotatably arranged on the support assembly on the corresponding side, and comprises a cam portion 1611 and a knob portion 1612 that are coaxially connected to each other. Specifically, the limiting mechanism 160 may be mounted on one side of the first support assembly 110, the cam portion 1611 of the cam-knob 161 and at least a part of the limiting member 162 may be accommodated within the first housing 113, and the knob portion 1612 of the cam-knob 161 is arranged outside the first housing 113. The cam-knob 161 may be mounted to the first back plate 1132 of the first housing 113 by means of a cam mounting member 163 such that the cam-knob 161 is fixed in position relative to the first back plate 1132. The limiting member 162 is provided with a cam hole 1623 for engagement with the cam portion 1611, and the cam hole 1623 and the cam portion 1611 each have a specific shape such that when the knob portion 1612 is rotated, the limiting member 162 can move up and down with the rotation of the cam portion 1611. One end of the limiting member 162 extends downwards and faces the rack 220, and is further provided with a plurality of snap teeth 1624 cooperating with the rack 220. Specifically, as shown in FIG. 13, the limiting member 162 comprises a first section 1621 extending downwards and a second section 1622 extending toward the bed body 200, the first section 1621 may extend to the bottom of the first back plate 1132, and the second section 1622 extends out of the first housing 113, with an end thereof extending into the track 210. The end of the second section 1622 is located directly below the rack 220 and is spaced apart from the rack 220 by a certain distance. An upper surface of the end of the second section 1622 is provided with a plurality of snap teeth 1624, and the snap teeth 1624 are shaped to match the plurality of teeth on the rack 220.

The limiting mechanism 160 is configured to control the meshing or separation of the snap teeth 1624 and the rack 220 by causing the cam portion 1611 to drive the limiting member 162 to move up and down by means of the knob portion 1612. The working principle of the limiting mechanism 160 of this embodiment is as follows: after the detection personnel adjusts the position of the position adjustment apparatus 100 in the length direction of the bed body 200, the position adjustment apparatus 100 is fixed to the desired position by operating the limiting mechanism 160, and then another two spatial dimensions of the detection device are adjusted by operating the outer rotating disk 1412 and the armrest 1372.

The magnetocardiography instrument 1 of this embodiment has the above-mentioned position adjustment apparatus 100, and in combination with the tracks 210, the rollers 150 and the limiting mechanism 160, the position of the detection device can be adjusted in three dimensional directions, namely the length direction, the width direction and the height direction, of the bed body 200. Therefore, the magnetocardiography instrument 1 of this embodiment can more accurately position the detection device to the optimal position required for measuring the magnetic field of the human body, and fix the detection device without affecting the high-sensitivity detection of the magnetic field, thereby greatly improving the practicality and operability of the magnetocardiography instrument 1.

Figure 14:
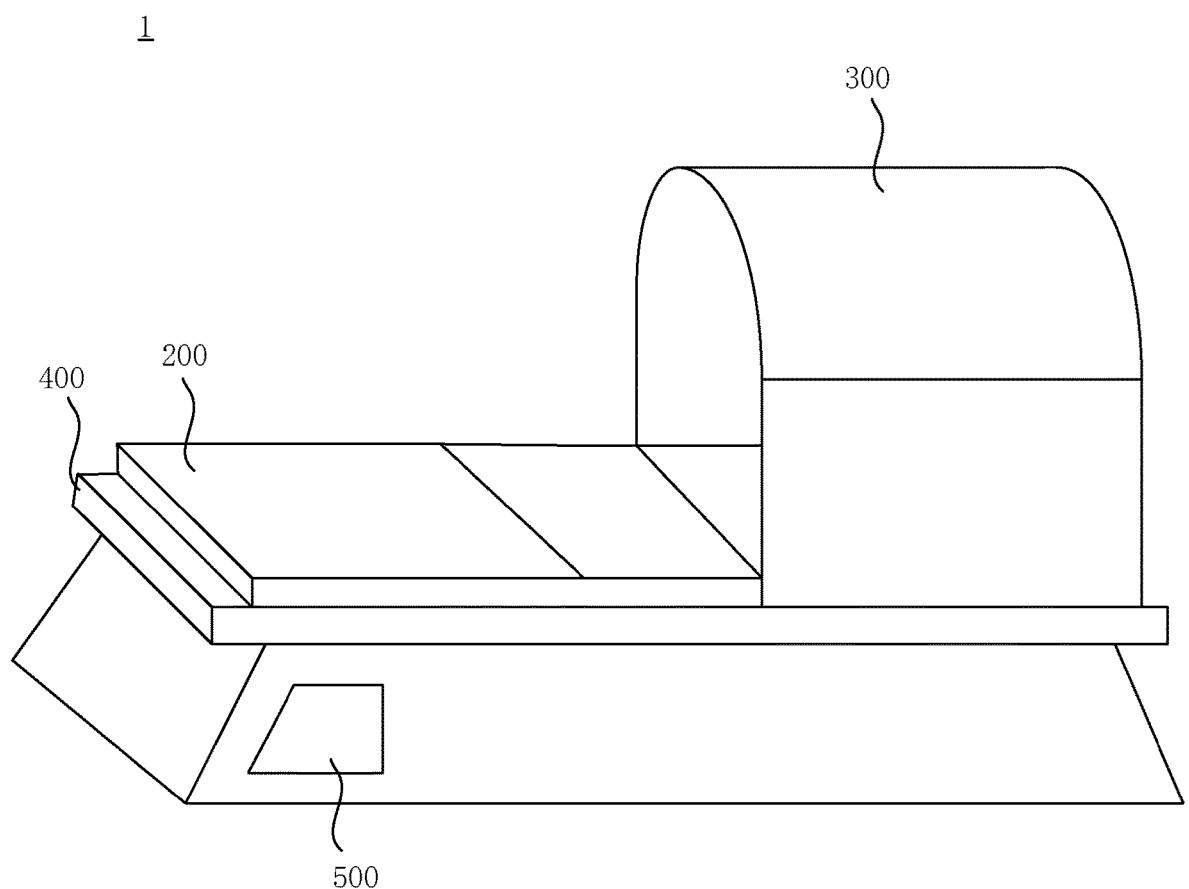
FIG. 14 shows a schematic view of the appearance of a magnetocardiography instrument according to an embodiment of the present disclosure.

FIG. 14 shows a schematic view of the appearance of a magnetocardiography instrument 1 according to an embodiment of the present disclosure. The magnetocardiography instrument 1 may further comprise a magnetic shielding cabin 300, a base 400, and an electric motor 500. The bed body 200 is arranged on the base 400, and the bed body 200 may be controlled by means of the electric motor 500 to slide in a length direction of the base 400 so as to drive the person to be detected to enter or leave the magnetic shielding cabin 300. When the magnetocardiography instrument 1 is in a non-working state, the position adjustment apparatus 100 may be located outside the magnetic shielding cabin 300. During use of the magnetocardiography instrument 1, the bed body 200 slides toward the inside of the magnetic shielding cabin 300 and reaches a predetermined position such that the position adjustment apparatus 100 is located inside the magnetic shielding cabin 300. In other words, the magnetic shielding cabin 300 covers the position adjustment apparatus 100 to prevent the detection process from being interfered by an external magnetic field. The electric motor 500 may preferably be arranged at the end of the base 400 remote from the magnetic shielding cabin 300 to prevent interference with the detection device.

The magnetic shielding cabin 300 is a magnetic shielding cylinder made of multiple layers of magnetic shielding materials. An outermost layer is made of an aluminum alloy for shielding high-frequency electromagnetic interference in the environment. The middle is a magnetic shielding cylinder made of multiple layers of high-permeability magnetic materials, for shielding low-frequency electromagnetic interference in the environment. An innermost layer and the portions between the different layers are nonmagnetic materials such as resin, plastic or nylon for providing support. The magnetic shielding cabin 300 is closed at one end and open at the other end to facilitate the entry and exit of the person to be tested. The magnetic shielding cabin 300 can further reduce interference of the external magnetic field to provide a good detection environment for the detection device. A demagnetizing coil may also be provided inside the magnetic shielding cabin 300, and the inside of the magnetic shielding cabin 300 is periodically demagnetized by using a degausser.

The magnetocardiography instrument 1 may further comprise: a magnetic compensation system. The magnetic compensation system is composed of a magnetic compensation coil and a high-precision current source, a noise signal of the ambient environment that is measured by the detection device is used as a reference signal, and the high-precision current source is used to apply a current to the magnetic compensation coil, so as to provide a magnetic field with an equivalent magnitude as an ambient interfering magnetic field and an opposite direction thereto for counteraction, thereby making the magnetic field in the magnetic shielding cabin 300 closer to zero. An air supply system and a non-magnetic light guide bar may also be provided inside the magnetic shielding cabin 300 to reduce the anxiety of the tested person in a semi-enclosed space and to improve the comfort of the tested person during measurement.

The magnetocardiography instrument 1 may further comprise a processing device and a storage device. The processing device is communicatively connected to the detection device to receive data detected by the detection device and generates a magnetocardiogram on the basis of the data. The storage device is connected to the processing device and used for storing the generated magnetocardiogram. The processing device may be various general-purpose and/or special-purpose processing components with processing and computing capabilities. Some examples of the processing device include, but are not limited to, a central processing unit (CPU), a graphics processing unit (GPU), various dedicated artificial intelligence (AI) computing chips, various computing units that run machine learning model algorithms, a digital signal processor (DSP), and any appropriate processor, controller, microcontroller, etc. The storage device may include, but is not limited to, a magnetic disk and an optical disk.

The working principle of the magnetocardiography instrument 1 is as follows: when the person to be detected is lying on the bed body, the position adjustment apparatus 100 and the tracks 210 are first operated such that the detection device is located at an optimal detection point directly above the heart of the human body. The person to be detected is then carried into the magnetic shielding cabin 300, the detection device is started, the data of magnetic field signals of the heart undergoes centralized collection, and the processing device uses relevant image generation software to generate a one-dimensional magnetocardiogram, a two-dimensional magnetocardiogram and a three-dimensional magnetocardiogram, thereby generating a magnetocardiography measurement report. Reading and discrimination may also be performed subsequently, and a diagnosis report may be generated.

It should be understood that, in this description, the orientations or positional relationships or dimensions denoted by the terms, such as "center", "longitudinal", "transverse", "length", "width", "thickness", "upper", "lower", "front", "rear", "left", "right", "vertical", "horizontal", "top", "bottom", "inner", "outer", "clockwise", "counterclockwise", "axial", "radial" and "circumferential", are the orientations or positional relationships or dimensions shown on the basis of the drawings, and these terms are used merely for ease of description, rather than indicating or implying that the device or element referred to must have particular orientations and be constructed and operated in the particular orientations, and therefore should not be construed as limiting the scope of protection of the present application.

In addition, the terms "first", "second" and "third" are merely for descriptive purposes and should not be construed as indicating or implying relative importance or implicitly indicating the number of technical features indicated. Thus, the features defined with "first", "second" and "third" may explicitly or implicitly comprise one or more features. In the description of the present application, the term "plurality of" means two or more, unless specifically and specifically limited otherwise.

In the present application, unless expressly stated or limited otherwise, the terms such as "mounting", "connection", "connected" and "fixing" should be interpreted broadly, for example, either fixed or detachable connection, or integration; which may be mechanical connection, or electrical connection, or communication; and which may be direct connection or indirect connection by means of an intermediate medium, and may be communication between the interiors of two elements or the interaction relationship of the two elements. For those of ordinary skills in the art, the specific meaning of the terms mentioned above in the present application may be construed according to specific circumstances.

In the present application, unless expressly stated or limited otherwise, the expression of the first feature being "above" or "below" the second feature may include the case that the first feature is in direct contact with the second feature, and may also include the case that the first and second features are not in direct contact but are contacted via another feature therebetween. Furthermore, the first feature being "over", "above" or "on" the second feature includes the case that the first feature is directly or obliquely above the second feature, or merely indicates that the first feature is at a higher level than the second feature. The first feature being "below", "under" or "beneath" the second feature includes the case that the first feature is directly or obliquely below the second feature, or merely indicates that the first feature is at a smaller level than the second feature.

This description provides many different embodiments or examples that can be used to implement the present application. It should be understood that these various embodiments or examples are purely illustrative and are not intended to limit the scope of protection of the present application in any way. On the basis of the disclosure of the description of the present application, those skilled in the art will be able to conceive of various changes or substitutions. Any changes or substitutions shall fall within the scope of protection of the present application. Therefore, the scope of protection of the present application shall be subject to the scope of protection of the claims.

What is claimed is:

1. A position adjustment apparatus for adjusting a position of a detection device, the position adjustment apparatus comprising:
   two support assemblies, each of the support assemblies comprising at least one support rod;
   a lifting frame arranged between the two support assemblies, the lifting frame having two ends respectively slidably connected to the support rods of the two support assemblies and being configured to move in a height direction of the support rods, the lifting frame comprising a mounting portion for mounting the detection device; and
   at least one height adjustment assembly arranged on at least one side of the lifting frame where one of the two support assemblies is located and configured to adjust a lifting height of the lifting frame, each height adjustment assembly of the at least one height adjustment assembly comprising
   a first pulley and a second pulley arranged in a height direction of the at least one support rod, and rotating shafts of the first pulley and the second pulley being both fixedly mounted on the support assembly arranged on the corresponding side of the lifting frame; and
   a drive belt wound around the first pulley and the second pulley, the lifting frame being fixedly connected to a predetermined position on the drive belt, the drive belt being configured to drive the lifting frame to move as the first pulley and the second pulley rotate.

2. The position adjustment apparatus according to claim 1, wherein each height adjustment assembly further comprises a locking mechanism, and the locking mechanism comprises:
- a fixed toothed disk fixedly arranged on the support assembly on the corresponding side of the lifting frame, wherein a hollow portion for accommodating at least a part of the first pulley is provided in the center of the fixed toothed disk, and a plurality of limiting teeth are arranged on an inside periphery of the hollow portion; and
- a limiting push piece slidably arranged on the first pulley and configured to slide in a radial direction of the first pulley, and the end of the limiting push piece facing the inside periphery of the hollow portion is further provided with complementary teeth that are complementary with the plurality of limiting teeth.

3. The position adjustment apparatus according to claim 2, wherein
the first pulley comprises an inner wheel and an outer rotating disk that are coaxial with each other, wherein
the drive belt is wound around the inner wheel and the second pulley, the outer rotating disk is accommodated in the hollow portion, and the limiting push piece is arranged on the outer rotating disk.

4. The position adjustment apparatus according to claim 3, wherein
the outer rotating disk is provided with a guide groove for accommodating the limiting push piece and allowing the limiting push piece to slide in a radial direction of the outer rotating disk.

5. The position adjustment apparatus according to claim 4, wherein
- a plurality of limiting protrusions and limiting recesses cooperating with the plurality of limiting protrusions are respectively provided at edges of two sides of the limiting push piece and an inner side of the guide groove, and the limiting push piece has a first position and a second position that are defined jointly by the limiting protrusions and the limiting recesses, and
- the locking mechanism is configured such that when the limiting push piece is pushed into the first position, the complementary teeth are meshed with at least some of the plurality of limiting teeth to lock the first pulley; and
- when the limiting push piece is pushed into the second position, the complementary teeth are separated from the plurality of limiting teeth to release the first pulley.

6. The position adjustment apparatus according to claim 3, wherein the support assembly arranged on the corresponding side of the lifting frame further comprises:
- a housing forming a cavity for accommodating the at least one support rod and the at least one height adjustment assembly; and
- a part of the housing corresponding to the outer rotating disk is provided with an opening for exposing at least a part of the outer rotating disk to the exterior of the housing.

7. The position adjustment apparatus according to claim 6, wherein the rotating shafts of the first pulley and the second pulley are both fixedly arranged on the housing of the corresponding support assembly.

8. The position adjustment apparatus according to claim 1, wherein the two support assemblies comprise a first support assembly and a second support assembly, and the lifting frame comprises:
- a first end plate slidably connected to the at least one support rod of the first support assembly;
- a second end plate slidably connected to the at least one support rod of the second support assembly; and
- at least one cross beam, two ends of each of the at least one cross beam being respectively connected to the first end plate and the second end plate.

9. The position adjustment apparatus according to claim 8, wherein
- one of the at least one height adjustment assembly is arranged on one side of the lifting frame where the first support assembly is located; and
- the first support assembly comprises two support rods arranged in parallel, and the one of the at least one height adjustment assembly is arranged between the two support rods; and
- the first end plate is fixedly provided with two sets of sleeves at the positions corresponding to the two support rods, and the sleeves of each set of sleeves are respectively fitted outside the corresponding support rods.

10. The position adjustment apparatus according to claim 9, wherein
the second support assembly comprises one support rod;
the second end plate is fixedly provided with a set of sleeves at the position corresponding to the one support rod, and the sleeves are fitted outside the one support rod.

11. The position adjustment apparatus according to claim 10, wherein the first end plate is further fixedly provided with an engagement portion, the engagement portion is provided with a slit allowing the drive belt to pass through, and the engagement portion is fixed to a predetermined position of the drive belt by means of a screw traversing the slit.

12. The position adjustment apparatus according to claim 10, wherein at least a part of an upper surface of each of the at least one cross beam is arranged tilted downwards in a direction from the first end plate to the second end plate.

13. The position adjustment apparatus according to claim 12, wherein the lifting frame further comprises:
- at least one structural reinforcing rope, two ends of each of the at least one structural reinforcing rope being respectively connected to two ends of one cross beam of the at least one cross beam; and
- the upper surface of the one cross beam is further provided with a wire guide groove for accommodating the at least one structural reinforcing rope.

14. The position adjustment apparatus according to claim 10, wherein the lifting frame further comprises:
- at least two sliding rods arranged in parallel, two ends of each of the at least two sliding rods being respectively directly or indirectly connected to the first end plate and the second end plate; and
- the mounting portion further comprises a plurality of sleeves, the plurality of sleeves being fitted on the at least two sliding rods such that the mounting portion slides along the at least two sliding rods.

15. The position adjustment apparatus according to claim 1, wherein the detection device comprises a plurality of magnetometer probes,
the mounting portion further comprises a mounting panel, and the mounting panel is provided with a plurality of slotted holes for mounting the plurality of magnetometer probes.

16. A magnetocardiography instrument, comprising:
a bed body;

the position adjustment apparatus of claim 1, wherein bottom ends of the two support assemblies of the position adjustment apparatus are respectively slidably connected to edges of two sides in a length direction of the bed body such that the position adjustment apparatus slides in the length direction of the bed body; and a plurality of magnetometer probes mounted on the mounting portion of the position adjustment apparatus.

17. The magnetocardiography instrument according to claim 16, wherein the bottom ends of the two support assemblies are further provided with a plurality of rollers; and the bed body is further provided with tracks at the positions corresponding to the bottom ends of the two support assemblies, the tracks extending in the length direction of the bed body for accommodating the plurality of rollers.

18. The magnetocardiography instrument according to claim 17, wherein the tracks are arranged on left and right sides of the bed body; and the plurality of rollers are arranged on the sides of the bottom ends of the support assemblies facing the bed body so as to be opposite the tracks.

19. The magnetocardiography instrument according to claim 18, wherein the bed body is further provided with a rack extending in the length direction thereof, and the position adjustment apparatus further comprises a limiting mechanism, wherein the limiting mechanism comprises:

a cam-knob rotatably arranged on either of the two support assembly assemblies and comprising a cam portion and a knob portion that are coaxially connected to the cam portion; and a limiting member provided with a cam hole for engagement with the cam portion, one end of the limiting member extending downwards and facing the rack, and the end being further provided with a plurality of snap teeth cooperating with the rack;

wherein the limiting mechanism is configured to control the meshing or separation of the snap teeth and the rack by causing the cam portion to drive the limiting member to move up and down by means of rotating the knob portion.

20. The magnetocardiography instrument according to claim 19, further comprising:

a base for bearing the bed body; and a magnetic shielding cabin arranged on the base, wherein the bed body is further configured to slide in a length direction of the base; and the magnetic shielding cabin is configured to cover the position adjustment apparatus when the bed body slides toward the magnetically shielded cabin to a predetermined position.

* * * * *